(12) United States Patent
Poynard (10) Patent No.: US 7,860,656 B2
(45) Date of Patent: Dec. 28, 2010

(54) DIAGNOSIS METHOD OF HEPATIC STEATOSIS USING BIOCHEMICAL MARKERS

(75) Inventor: Thierry Poynard, Paris (FR)

(73) Assignee: Assistance Publique-Hopitaux de Paris (Ap-Hp), Paris (FR)

( * ) Notice: Subject to any disclaimer, the term of this patent is extended or adjusted under 35 U.S.C. 154(b) by 1132 days.

(21) Appl. No.: 11/050,396

(22) Filed: Feb. 3, 2005

(65) Prior Publication Data

US 2006/0173629 A1 Aug. 3, 2006

(51) Int. Cl.
G01N 33/50 (2006.01)
(52) U.S. Cl. .......................................... 702/19; 600/322
(58) Field of Classification Search .................. None
See application file for complete search history.

(56) References Cited

U.S. PATENT DOCUMENTS 6,631,330 B1 * 10/2003 Poynard ...................... 702/19
2006/0172286 A1 * 8/2006 Poynard ...................... 702/19

OTHER PUBLICATIONS

Day et al. (Hepatology, p. 1463-1466, Jun. 1998).*
Rinella et al. (Liver Transplantation, vol. 7, No. 5, p. 409-414, May 2001).*
Burt (Current Diagnostic Pathology, vol. 7, p. 141-147, 2001).*
Lu et al. (world Journal of Gastroenterology, vol. 9, No. 3, p. 2796-2800, 2003).*
Chitturi et al. (Hepatology, vol. 36, No. 2, p. 403-409, 2002).*
Chan et al. (International Journal of Obesity, vol. 28, 1257-1263, 2004).*
Duhamel et al. (Hepatology, vol. 4, No. 4, p. 577-585, 1984).*
Koruk et al. (Turkish journal of Gastroenterology, vol. 14, No. 1, p. 12-17, 2003).*
AASLD Abstracts, Hepatology, 34:4 Suppl., October, 510A-511A (2003).
Angulo, "Nonalcoholic Fatty Liver Disease," N Engl J Med, vol. 346, No. 16, 1221-1231 (Apr. 18, 2002).
Bellentani et al., "Prevalence of and Risk Factors for Hepatic Steatosis in Northern Italy," Ann Intern Med, 132(2):112-117 (2000).
Bravo et al., "Liver Biopsy," N Engl J Med, 344(7):495-500 (2001).
Browning et al., "Molecular mediators of hepatic steatosis and liver injury," J Clin Invest, 114(2):147-152 (2004).
Callewaert et al., "Noninvasive diagnosis of liver cirrhosis using DNA sequencer-based total serum protein glycomics," Nat Med, 10(4):429-434 (2004).
Dam-Larsen et al., "Long term prognosis of fatty liver: risk of chronic liver disease and death," Gut, 53(5):750-755 (2004).
Day, "Pathogenesis of steatohepatitis," Best Pract Res Clin Gastroenterol, 16(5):663-678 (2002).
El-Serag et al., "Diabetes Increases the Risk of Chronic Liver Disease and Hepatocellular Carcinoma," Gastroenterology, 126(2):460-468 (2004).

Fabris et al., "Alcohol is an important co-factor for both steatosis and fibrosis in Northern Italian patients with chronic hepatitis C," J Hepatol, 41(4):644-651 (2004).
Imbert-Bismut et al., "Intralaboratory analytical variability of biochemical markers of fibrosis (Fibrotest) and activity (Actitest) and reference ranges in healthy blood donors," Clin Chem Lab Med, 42(3):323-333 (2004).
Levitsky et al., "Diagnosis and Therapy of Alcoholic Liver Disease," Seminars in Liver Dis, 24(3):233-247 (2004).
Munteanu et al., Intra-individual fasting versus postprandial variation of biochemical markers of liver fibrosis (FibroTest) and activity (ActiTest), Comparative Hepatology, 3:3 (2004).
Myers et al., "Prediction of liver histological lesions with biochemical markers in patients with chronic hepatitis B," Journal of Hepatology, 39(2):222-230 (2003).
Naveau et al., "Biomarkers for the Prediction of Liver Fibrosis in Patients With Chronic Alcoholic Liver Disease," Clin Gastroenterol and Hepatol, 3(2):167-174 (2005).
Phillips et al., "Post-transplant Recurrent Hepatitis B Viral Liver Disease; Viral-burden, Steatoviral, and Fibroviral Hepatitis B," Am Journal of Pathol,140(6):1295-1308 (1992).
Poynard et al., "Effect of Treatment With Peginterferon or Interferon Alfa-2b and Ribavirin on Steatosis in Patients Infected With Hepatitis C," Hepatology, 38(1):75-85 (2003).
Poynard et al., "Overview of the diagnostic value of biochemical markers of liver fibrosis (FibroTest, HCV FibroSure) and necrosis (ActiTest) in patients with chronic hepatitis C," Comp Hepatol, 3(1):8 (2004).
Poynard et al., "Prospective Analysis of Discordant Results between Biochemical Markers and Biopsy in Patients with Chronic Hepatitis C," Clin Chem, 50:8 1344-1355 (2004).
Sørensen et al., "Prospective Evaluation of Alcohol Abuse And Alcoholic Liver Injury in Men As Predictors Of Development Of Cirrhosis," The Lancet, 2(8397):241-244 (1984).
Angulo, "Nonalcoholic Fatty Liver Disease," N Engl J Med, 346(16):1221-1231 (2002).
Annoni et al., "Serum Type III Procollagen Peptide and Laminin (Lam-P1) Detect Alcoholic Hepatitis in Chronic Alcohol Abusers," Hepatology, 9(5):693-697 (1989).
Bedossa et al., "Observer Variation in Assessment of Liver Biopsies of Alcoholic Patients," Alcohol Clin Exp Res, 12(1):173-178 (1988).
Bellentani et al., "Prevalence of and Risk Factors for Hepatic Steatosis in Northern Italy," Ann Intern Med, 132(2):112-117 (2000).
Castera et al., "Serum Laminin and Type IV Collagen are Accurate Markers of Histologically Severe Alcoholic Hepatitis in Patients with Cirrhosis," J Hepatol, 32(3):412-418 (2000).
Chossegros, "Extracellular Martix Serum Markers (ECMSM) in Alcoholic Liver Disease," J Hepatol, 22(2):96-99 (1995).
Halfon et al., "A Prospective Assessment of the Inter-Laboratory Variability of Biochemical Markers of Fibrosis (Fibro Test) and Activity (ActiTest) in Patients with Chronic Liver Disease," Comparative Hepatology, 1(3):1-10 (2002).

(Continued)

Primary Examiner—Karlheinz R Skowronek
(74) Attorney, Agent, or Firm—Ballard Spahr LLP (57) ABSTRACT

The present invention is drawn to a new diagnosis method for detecting the extent of hepatic steatosis in a patient, in particular in a patient who suffers from a disease involving hepatic steatosis, or who already had a positive diagnosis test of liver fibrosis and/or presence of liver necroinflammatory lesions, by using the serum concentration of easily detectable biological markers. The invention is also drawn to diagnosis kits for the implementation of the method.

11 Claims, 5 Drawing Sheets

OTHER PUBLICATIONS

Maher, "Alcoholic Steatosis and Steatohepatitis," *Seminars in Gastrointest Dis*, 13(1):31-39 (2002).

Mathurin et al., "Survival and Prognostic Factors in Patients with Severe Alcoholic Hepatitis Treated with Prednisolone," *Gastroenterology*, 110(6):1847-1853 (1996).

Mathurin et al., "Corticosteroids Improve Short-Term Survival in Patients with Severe Alcoholic Hepatitis (AH): Individual Data Analysis of the Last Three Randomized Placebo Controlled Double Blind Trials of Corticosteroids in Severe AH," *Journal of Hepatology*, 36(4):480-487 (2002).

Nøjgaard et al., "Serum Levels of YKL-40 and PIIINP as Prognostic Markers in Patients with Alcoholic Liver Disease", *Journal of Hepatology*, 39(2):179-186 (2003).

Naveau et al., "Alpha-2-Macroglobulin and Hepatic Fibrosis," *Digestive Disease and Sciences*, 39(1):2426-2432 (1994).

Poynard et al., "The Diagnostic Value of Biomarkers (SteatoTest) for the Prediction of Liver Steatosis," *Comparative Hepatology*, 4(10):1-14 (2005).

Poynard et al., "Evaluation of Efficacy of Liver Transplantation in Alcoholic Cirrhosis Using Matched and Simulated Controls: 5 Year Survival," *Journal of Hepatology*, 30:1130-1137 (1999).

Browning et al., "Molecular Mediators of Hepatic Steatosis and Liver Injury," *The Journal of Clinical Investigation*, 114(2): 147-152 (2004).

Munteanu et al., "Noninvasive Biomarkers for the Screening of Fibrosis, Steatosis and Steatohepatitis in Patients with Metabolic Risk Factors: Fibro Test-FibroMax™ Experience," *J Gastrointestin Liver Dis*, 17(2): 187-191 (2008).

Poynard et al., "The Diagnostic Value of Biomarkers (SteatoTest) for the Prediction of Liver Steatosis," *Comparative Hepatology*, 4(10): 1476-5926 (2005).

U.S. Appl. No. 11/050,638, filed Feb. 3, 2005, Poynard, Request for Continued Examination and Response to Office Action, Mar. 31, 2010.

U.S. Appl. No. 11/050,638, filed Feb. 3, 2005, Poynard, Notice of Appeal, Feb. 3, 2010.

U.S. Appl. No. 11/050,638, filed Feb. 3, 2005, Poynard, Advisory Action, Nov. 24, 2009.

U.S. Appl. No. 11/050,638, filed Feb. 3, 2005, Poynard, Response to Final Office Action, Nov. 2, 2009.

\* cited by examiner

DIAGNOSIS METHOD OF HEPATIC STEATOSIS USING BIOCHEMICAL MARKERS

FIELD OF THE INVENTION

The present invention is drawn to a new diagnosis method for detecting the extent of hepatic steatosis in a patient, in particular in a patient who suffers from a disease involving hepatic steatosis or who already had a positive diagnosis test of liver fibrosis and/or presence of liver necroinflammatory lesions, by using the serum concentration of easily detectable biological markers. The invention is also drawn to diagnosis kits for the implementation of the method.

BACKGROUND OF THE INVENTION

Fatty liver, also named hepatic steatosis, is defined as an excessive accumulation of fat in hepatocytes (Bravo A A, et al. N. Engl. J. Med. 2001:344; 495-500; Angulo P. N. Engl. J. Med. 2002 Apr. 18; 346(16):1221-31). Fatty liver disease involves the accumulation of triglycerides in hepatocytes, necrosis of hepatocytes, inflammation (Day C P. Best Pract. Res. Clin. Gastroenterol. 2002; 16:663-78; Browning J D, Horton J D. J. Clin. Invest. 2004; 114:147-52), small hepatic veins obliteration and often fibrosis with sometimes progression to cirrhosis, hepatocellular cancer and liver-related death (El-Serag H B, et al. Gastroenterology 2004; 126:460-468, Dam-Larsen S, et al. Gut 2004; 53:750-5).

Worldwide the prevalence of hepatic steatosis is very high, associated with several factors such as alcohol, diabetes, overweight, hyperlipidemia, insulin resistance, hepatitis C genotype 3, abetalipoproteinemia and some drugs (Bellentani S, et al. Ann. Intern. Med. 2000; 132:112-7; Levitsky J, Mailliard M E. Semin. Liver Dis. 2004; 24:233-47).

Non-alcoholic fatty liver disease (NAFLD), is an adaptive response of the liver to insulin resistance that can trigger non-alcoholic steatohepatitis (NASH), which can itself induce a fibrogenic response that can result in cirrhosis (Day C P. Best Pract. Res. Clin. Gastroenterol. 2002; 16:663-78).

In patients with alcoholic liver disease (Sorensen T I, et al. Lancet. 1984; 2:241-4), chronic hepatitis C (Fabris P, et al. J. Hepatol. 2004; 41:644-51), and perhaps in hepatitis B (Phillips M J, et al. Am. J. Pathol. 1992; 140:1295-308), the presence of hepatic steatosis is also associated with fibrosis progression, with or without associated necroinflammatory lesions (alcoholic or viral hepatitis).

There is no standard recommendation for the diagnosis of hepatic steatosis. The usual recommendation is to measure GGT and ALT and to perform liver biopsy for the grading and staging (Bellentani S, et al. Ann. Intern. Med. 2000; 132:112-7; Levitsky J, Mailliard M E. Semin. Liver Dis. 2004; 24:233-47; Bravo A A, et al. N. Engl. J. Med. 2001:344; 495-500). As liver biopsy is still an invasive and costly procedure, with a potential sampling error, it could be advantageous to have a fast and easy to perform test that would give a good predictive value of the level of hepatic steatosis in the patient.

For the diagnosis of fibrosis, non-invasive FibroTest (FT) (Biopredictive, Paris France, U.S. Pat. No. 6,631,330) has been validated as surrogate marker in chronic hepatitis C (Poynard T, et al. Comp Hepatol. 2004; 3:8) and B (Myers R P, et al. J Hepatol. 2003; 39:222-30) and recently in alcoholic liver disease (Callewaert N, et al. Nature Med 2004; 10; 1-6; Naveau S, et al. Clin Gastroenterol Hepatol in press).

So far, however, no study has demonstrated that a single or a panel of biomarkers can be used as an alternative to liver biopsy for the diagnosis of hepatic steatosis in the most common causes: alcohol, viral hepatitis and NAFLD.

There is therefore a need to develop a diagnosis method that would give a good predictive value of the extent of hepatic steatosis in a patient, and that would be reliable enough to reduce the need of liver biopsy. This method would be particularly advantageous for a patient who suffers from a disease involving hepatic steatosis or who already had a positive diagnostic test of liver fibrosis or necroinflammatory lesions, to adapt the treatment to his precise disease.

SUMMARY OF THE INVENTION

The present invention provides a method of diagnosis that assesses prospectively the predictive value of a combination of simple serum biochemical markers for the diagnosis of hepatic steatosis, in particular in the liver of a patient who suffers from a disease involving hepatic steatosis or who already had a positive diagnosis test of liver fibrosis and/or presence of liver necroinflammatory lesions. With the reach of high positive predictive values (prediction of significant hepatic steatosis) or negative predictive values, the number of biopsy indications could be reduced. This could be useful for patients and society in order to reduce the cost and the risk of liver biopsies.

DESCRIPTION OF THE FIGURES

FIG. 2: Relationship between SteatoTest, GGT (IU/L) and ALT (IU/L) and the grade of liver steatosis.

Notched box plots showing the relationship in the training group (FIG. 2A); in validation group 1, HCV patients before treatment (FIG. 2B); in validation group 2, cured HCV patients (FIG. 2C); in validation group 3, alcoholic liver disease (FIG. 2D); and in controls, healthy volunteers fasting and non-fasting and non-fasting blood donors (FIG. 2E).

The horizontal line inside each box represents the median and the width of each box the median±1.57 interquartile range/$\sqrt{n}$ to assess the 95% level of significance between group medians. Failure of the shaded boxes to overlap signifies statistical significance (P<0.05). The horizontal lines above and below each box encompass the interquartile range (from $25^{th}$ to $75^{th}$ percentile), and the vertical lines from the ends of the box encompass the adjacent values (upper: $75^{th}$ percentile plus 1.5 times interquartile range, lower $25^{th}$ percentile minus 1.5 times interquartile range). In validation group 3, almost all patients had steatosis and group S0 and S1 were combined.

Failure of the shaded boxes to overlap signifies statistical significance between medians (P<0.05). There was a significant difference between all grades by Tukey-Kramer multiple comparison test for all pairwise differences between means (P<0.05).

For GGT and ALT there was no significant difference between "No steatosis" and "<5%" and between "5-33%" and "33-100%". For ALT there was also no significant difference between "No steatosis" and "5-33%", "<5%" and "5-33%".

DESCRIPTION OF THE PREFERRED EMBODIMENTS

The present invention is therefore drawn to a method for diagnosis of hepatic steatosis in a patient or from a serum or a plasma sample from a patient, comprising the steps of:

a) studying 5 biochemical markers by measuring the values of their concentration in the serum or plasma of said patient, wherein said markers are:
 ApoA1 (apolipoprotein A1),
 alpha.2-macroglobulin,
 ALT (alanine aminotransferase),
 GGT (gammaglutamyl transpeptidase), and
 Triglycerides;

b) studying one clinical marker chosen in the group constituted of the body mass index (Weight/Height$^2$), the waist measurement, and the (waist measurement/hip measurement) ratio;

c) combining said values through a logistic function including said markers in order to obtain an end value, wherein said logistic function is obtained through the following method:

i) classification of a cohort of patients in different groups according to the extent of their disease;

ii) identification of factors which differ significantly between these groups by unidimensional analysis;

iii) logistic regression analysis to assess the independent discriminative value of markers for the diagnosis of hepatic steatosis;

iv) construction of the logistic function by combination of these identified independent factors; and d) analyzing said end value of said logistic function in order to determine the presence of hepatic steatosis in said patient.

Hepatic steatosis may be associated with several factors such as alcohol, diabetes, overweight, hyperlipidemia, insulin resistance, hepatitis C genotype 3, abetalipoproteinemia and some drugs. In particular, the present invention is directed to the diagnosis of both alcoholic and non-alcoholic steatosis.

By definition the best index ("Steatosis score") in term of discrimination was the logistic regression function combining the independent factors.

The logistic function is obtained by combining the relative weight of each parameter, as individually determined in the logistic regression, with a negative sign when the markers harbor a negative correlation with the stage of hepatic steatosis. Logarithms are used for markers whose values have a very large range.

The quality of the logistic function is analyzed with the aid of a Receiver Operating Characteristic (ROC) curve that is obtained depending on the threshold desired for the diagnosis. The way of obtaining the ROC curve is described in the examples. In the present invention, the classification of the patients was done according to the different grades of hepatic steatosis (none=0%, mild=1-5%, moderate=6-32%, and (marked and severe)=33-100%, wherein each percentage refers to the percentage of hepatocytes involved in steatosis), but it could be changed if diagnosis of patient only with an marked or severe grade was intended. This would lead to another ROC curve.

The diagnosis of the presence or absence hepatic steatosis in the patient can be further refined by the data concerning the expected prevalence of hepatic steatosis in the population.

The logistic function may further comprise other clinical or biochemical markers. In a preferred embodiment, the logistic function also comprises the age and gender of the patient. In another embodiment, the logistic function may also comprise other biochemical markers, such as total bilirubin, haptoglobin, AST (aspartate aminotransferase), glucose, and (cholesterol or HDL-cholesterol). Preferably, the logistic function will comprise at least 1 or 2, more preferably 3 to 5 of these other biochemical markers. Most preferably, the logistic function may also comprise total bilirubin, haptoglobin, glucose, and cholesterol.

The biochemical markers that are dosed in step a) of the method according to the present invention are "simple" biochemical markers, which means that they are easily dosed with methods already known in the art (chromatography, electrophoresis, ELISA assay . . . ).

The different coefficients used for the values obtained for the different markers in the logistic function can be calculated through statistical analysis, as described in the examples.

In particular, a suitable logistic function that can be used for the implementation of the method of the invention is as follows:

$f = a1 - a2.[Age(years)] + a3.[ApoA1(g/L)] - a4[Body Mass Index(Weight/Height^2)] + a5.Log [.alpha.2-macroglobulin(g/L)] - a6.Log [ALT(alanine aminotransferase)(IU/L)] - a7.Log [total bilirubin (\mu mol/L)] - a8.[cholesterol(mmol/L)] - a9.Log [GGT(gammaglutamyl transpeptidase)(IU/L)] - a10.[glucose(mmol/L)] - a11.Log [Haptoglobin (g/L)] - a12.[triglycerides(mmol/L)] + a13.[Gender (female=0,male=1)]$, with a1 comprised in the interval of [6.68805−x %; 6.68805+x %], a2 comprised in the interval of [1.55337E-02−x %; 1.55337E-02+x %], a3 comprised in the interval of [1.161531−x %; 1.161531+x %], a4 comprised in the interval of [0.11889−x %; 0.11889+x %], a5 comprised in the interval of [1.74791−x %; 1.74791+x %], a6 comprised in the interval of [0.96453−x %; 0.96453+x %], a7 comprised in the interval of [0.11958−x %; 0.11958+x %], a8 comprised in the interval of [0.68125−x %; 0.68125+x %], a9 comprised in the interval of [1.17922−x %; 1.17922+x %], a10 comprised in the interval of [1.46963−x %; 1.46963+x %], a11 comprised in the interval of [0.34512−x %; 0.34512+x %], a12 comprised in the interval of [1.17926−x %; 1.17926+x %], and a13 comprised in the interval of [0.35052−x %; 0.35052+x %].

An "interval of [a−x %; a+x %]" means an interval of [(100−x)/100.a; (100+x)/100a]. Preferably, x is at most 90, 80 or 70, more preferably at most 60, 50, or 40, even more preferably at most 30, 20, 10 or 5. All $a_i$ coefficients are truncated to a number of 5 decimals. For instance, for x equal to 90, a13 is comprised in the interval of [0.03505; 0.66598].

Indeed, the numerical definitions for the coefficients in the different functions can vary depending on the number and characteristics of the patients studied. Therefore, the value given for the coefficients of the different markers have to be interpreted as capable to being slightly different, without reducing the scope of the invention.

A specific usable function, when x is equal to zero, is:

$f = 6.68805 - 1.55337E\text{-}02 \cdot [\text{Age(years)}] + 1.161531 \cdot [\text{ApoA1(g/L)}] - 0.11889 \cdot [\text{Body Mass Index (Weight/Height}^2)] + 1.74791 \cdot \text{Log}[\alpha.2\text{-macroglobulin(g/L)}] - 0.96453 \cdot \text{Log}[\text{ALT(alanine aminotransferase)(IU/L)}] - 0.11958 \cdot \text{Log}[\text{total bilirubin}(\mu\text{mol/L})] - 0.68125 \cdot \text{Log}[\text{cholesterol (mmol/L)}] - 1.17922 \cdot \text{Log}[\text{GGT(gammaglutamyl transpeptidase)(IU/L)}] - 1.46963 \cdot \text{Log}[\text{glucose (mmol/L)}] - 0.34512 \cdot \text{Log}[\text{Haptoglobin(g/L)}] - 1.17926 \cdot \text{Log}[\text{triglycerides(mmol/L)}] + 0.35052 \cdot [\text{Gender(female}=0,\text{male}=1)]$.

Depending on the end value obtained by the analysis of biological markers values with the logistic function, it is possible to draw conclusions about the presence or absence of hepatic steatosis for the patient. It is also possible to conclude about the grade of hepatic steatosis, by taking said grade as the threshold in the drawing of the ROC curve.

In certain embodiments, the invention thus concerns a method as previously described, wherein the end value of the logistic function is further used for the diagnosis of hepatic steatosis grade. The different grades of hepatic steatosis are defined according to histological features of liver biopsies. A more precise definition of hepatic steatosis grades is provided in Example 1.

The method according to the invention may further comprise a step of prediction of the evolution of the disease, based on the hepatic steatosis grade deducted from the end value of the logistic function. In particular, a Steatosis score at the 0.30 cut off has a very high sensitivity ranging from 85% to 100% according to different groups (Table 4) and a Steatosis score at the 0.70 cutoff has a very high specificity ranging from 83% to 100%. Furthermore as already demonstrated for Fibrotest (Poynard 2004 Clin Chem 2004) many of the discordances between Steato-score and biopsy were due to error of the biopsy (small sample size). It is expected that the method of the invention will reduce the need of liver biopsy by more than 80%. For the first time, a clinician can have an estimate of major histological features leading to cirrhosis or explaining liver tests abnormalities: Steatosis score for steatosis, Fibrosis score (FibroTest, Biopredictive, Paris, France) for fibrosis, Activity score (ActiTest, Biopredictive, Paris, France) for the necrotico-inflammatory features of chronic hepatitis C and B. Biopsy should be indicated only in second line in case of non interpretable components as described for the Fibrosis score (FibroTest), i.e acute inflammation, Gilbert syndrome or hemolysis (Poynard Clin Chem 2004).

According to the invention, the hepatic steatosis grade deducted from the end value of the logistic function can also be very valuable for the physician to choose a suitable treatment for the patient, according to the stage of the disease.

Also, said hepatic steatosis grade may be used by the physician to decide whether to perform a liver biopsy on the patient or not.

Depending of the prevalence of hepatic steatosis in the population of patients that are consulting, the data obtained with the method of the invention can be used to determine the need to perform a liver biopsy on the patient. It is expected that the method of the invention will reduce the need of liver biopsy by around 80%.

The method of the invention is intended to be used for patients suffering of any disease involving hepatic steatosis, that could develop to cirrhosis. By a "disease involving hepatic steatosis" is meant any disease that may lead to the development of hepatic steatosis. In particular, the method of the invention is advantageously performed for detecting hepatic steatosis in patients suffering from a disease included in the group consisting of hepatitis B and C, alcoholism, hemochromatosis, metabolic disease, diabetes, obesity, autoimmune hepatitis, primary biliary cirrhosis, .alpha.1-antitrypsin deficit, Wilson disease.

The method of the invention is particularly intended to be used for a patient who was already subjected to a diagnosis test of liver fibrosis and/or presence of liver necroinflammatory lesions.

More preferably, the method of the invention is intended to be used for a patient who was already subjected to a FibroTest/Acti-Test diagnostic test, as described in U.S. Pat. No. 6,631,330, which is herein incorporated by reference.

The invention is also drawn to a kit of diagnosis of hepatic steatosis in a patient, comprising instructions allowing to determine the presence or absence of hepatic steatosis in said patient, after dosage of biochemical markers.

The instructions may comprise the logistic function that has to be used after determination of the dosage of the biochemical markers. It can appear as a printed support as well as a computer usable support, such as a software. The instructions may also comprise the ROC curve depending of the threshold that is looked for, to allow the analysis of the end data obtained from the logistic function. They may also comprise different tables that allow to obtain the predictive values, depending of the expected prevalence of hepatic steatosis in the patient population.

The diagnosis kit according to the present invention may also contain elements allowing the dosage of the biological markers of interest.

Said diagnosis kit may also contain instructions for the quantification of hepatic steatosis different grades (none=0%, mild=1-5%, moderate=6-32%, marked=33-66% and severe=67-100%), and other intermediate grades.

The method of the invention can easily be automated, the dosage of the markers being performed automatically, the data being sent to a computer or a calculator that will calculate the value of the logistic function and analyze it with the aid of the ROC curve, and eventually the prevalence of hepatic steatosis in the patient population. The data obtained by the physician is therefore more easily interpretable, and will allow for an improvement in the process for deciding the need of a biopsy or the adequate treatment to prescribe.

The following examples are meant to describe an aspect of invention, and give the methodology in order to repeat the method of the invention, but shall not be limiting the invention.

EXAMPLES

Example 1

Patients and Methods 1.1. Patients

Figure 1:
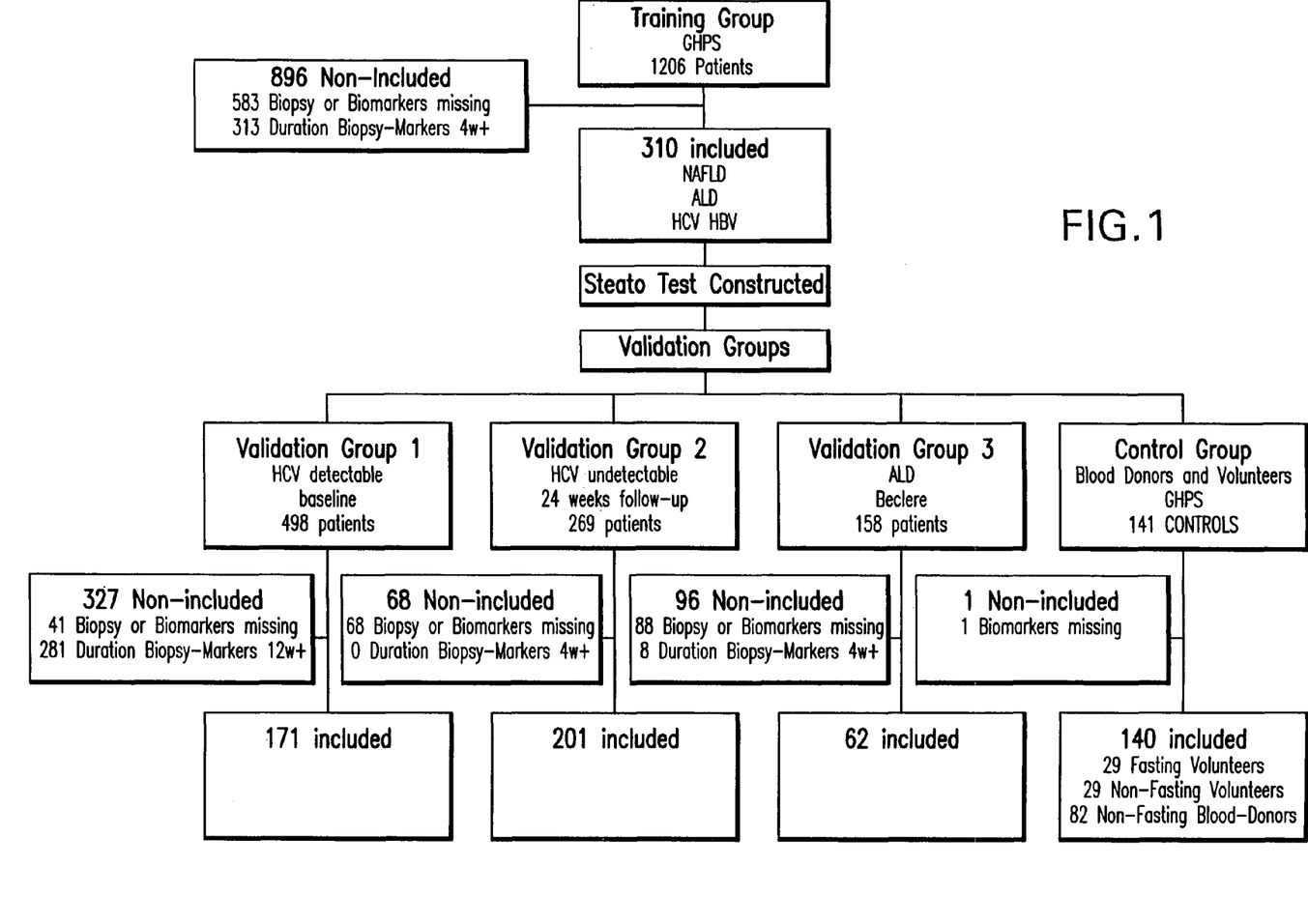
FIG. 1: Flow chart of patients analyzed and included in the training and validation groups.

Consecutive patients with available serum, a consistent liver biopsy and a duration of time between serum and biopsy shorter than 3 months were included (FIG. 1). Non-inclusion criteria included non-available serum, and non-available biopsies and patients because biopsy and serum were collected more than 3 month apart. The analysis was performed on a first group (training group) and validated on 3 different groups (validation groups).

Training group patients were retrospectively included for this specific analysis, but have been analyzed in previous prospective validation studies of Fibrotest between September 2000 and August 2004 (Poynard T, et al. Comp. Hepatol. 2004; 3:8; Myers R P, et al. J Hepatol. 2003; 39:222-30;

Ratziu V, et al. Hepatology 2003; 38:510A). All were inpatients hospitalized in the Department of Hepato-Gastroenterology of Groupe Hospitalier Pitié-Salpêtrière for NAFLD, hepatitis C, B, and alcoholic liver disease.

Validation group 1 patients (hepatitis C patients) were retrospectively analyzed from a study of hepatic steatosis in patients with chronic hepatitis C (Poynard T, et al. Hepatology. 2003; 38:75-85). For this purpose, previously non-treated patients of a prospective multicentre randomized trial of PEG-IFN and Ribavirin were included. The biomarkers and the biopsy results at baseline were used.

Validation group 2 patients (former Hepatitis C with undetectable HCV patients) were the patients of the same randomized trial as in validation group 1 (Poynard T, et al. Hepatology. 2003; 38:75-85), who have been "cured" with sustained virologic response, meaning that HCV RNA is undetectable 24 weeks after the end of the treatment. The biomarkers and the biopsy results performed 24 weeks after the end of the treatment were used. This group has been considered as a validation group of NAFLD because possible viral steatosis has been cured by the treatment (Poynard T, et al. Hepatology. 2003; 38:75-85).

Validation group 3 patients (alcoholic liver disease patients) were retrospectively included for this specific analysis, but were prospectively included between 1998 and 2000 in a cohort of alcoholic patients for which one primary endpoint was the identification of biochemical markers. The details of this cohort have been recently published in a validation study of FibroTest (Naveau S, et al. Clin. Gastroenterol. Hepatol. 2005 in press). All were inpatients hospitalized in the Hepato-Gastroenterology Department of Hôpital Antoine Béclère for complications of alcoholic liver disease.

Patients' characteristics of the different groups are listed in Table 1.

TABLE 1

Characteristics of included patients

| Characteristics | Training group | Validation group 1 HCV | Validation group 2 HCV cured | Validation group 3 Alcoholic liver disease |
|---|---|---|---|---|
| Number of patients | 310 | 171 | 201 | 62 |
| Age at biopsy (years) | 48.9 (12.4) | 44.1 (7.2) | 43.6 (8.0) | 46.6 (9.8) |
| Male | 201 (65%) | 111 (65%) | 122 (61%) | 47/62 (76%) |
| Female | 109 (35%) | 60 (35%) | 79 (39%) | 15 (24%) |
| BMI (kg/m2) | 25.4 (5.1) | 27.7 (5.0) | 26.5 (4.8) | 24.2 (4.1) |
| Biopsy quality | | | | |
| Length | 17.0 (6.2) | 16.6 (15.5) | 17.0 (8.2) | 13.5 (6.8) |
| Length >= 15 mm | 205 (67%) | 82 (48%) | 96 (48%) | 15 (24%) |
| Number of fragments | 2.5 (2.3) | — | — | 1.9 (1.6) |
| One fragment | 128/278 (46%) | — | — | 37 (60%) |
| Duration biopsy-serum, mean (days range) | 1 (0-30) | 40 (0-90) | 11 (0-45) | 7 (0-14) |
| Liver Risk factor | | | | |
| HCV | 211 (68%) | 171 (100%) | 0 (0%) | 0 (0%) |
| HBV | 18 (6%) | 0 (0%) | 0 (0%) | 0 (0%) |
| NAFLD | 69 (22%) | 0 (0%) | 0 (0%) | 0 (0%) |
| ALD | 12 (4%) | 0 (0%) | 0 (0%) | 0 (0%) |
| Daily alcohol >= 50 g/day | 34/236 (14%) | 0 (0%) | 0 (0%) | 62 (100%) |
| Cured HCV infection | 0 (0%) | 0 (0%) | 201 (100%) | 0 (0%) |
| Metabolic factor | | | | |
| BMI >= 27.0 | 92 (30%) | 88 (51%) | 77 (38%) | 14 (23%) |
| Glucose >= 6.0 mmol/L | 63 (20%) | 30 (18%) | 27 (13%) | 20 (32%) |
| Triglycerides >= 1.7 mmol/L | 67 (22%) | 36 (21%) | 54 (27%) | 20 (32%) |
| Cholesterol >= 6.0 mmol/L | 61 (20%) | 12 (7%) | 26 (13%) | 23 (37%) |
| Metabolic factor: number per patient | | | | |
| None | 132 (43%) | 60 (35%) | 96 (48%) | 17 (27%) |
| One | 101 (33%) | 64 (37%) | 72 (36%) | 20 (32%) |
| Two | 52 (17%) | 39 (23%) | 31 (15%) | 19 (31%) |
| Three | 22 (7%) | 8 (5%) | 0 (0%) | 5 (8%) |
| Four | 3 (1%) | 0 (0%) | 2 (1%) | 1 (2%) |
| Liver steatosis grade | | | | |
| None (0%) | 130 (42%) | 58 (34%) | 116 (58%) | 2 (3%) |
| Mild (Score 1-5%) | 40 (13%) | 68 (40%) | 63 (31%) | 2 (3%) |
| Moderate (Score 6-33%) | 69 (22%) | 35 (20%) | 17 (8%) | 42 (68%) |

TABLE 1-continued

Characteristics of included patients

| Characteristics | Training group | Validation group 1 HCV | Validation group 2 HCV cured | Validation group 3 Alcoholic liver disease |
|---|---|---|---|---|
| Marked (Score 34-66%) | 36 (12%) | 7 (4%) | 4 (3%) | 12 (19%) |
| Severe (Score 67-100%) | 35 (11%) | 3 (2%) | 1 (0.5%) | 4 (7%) |
| Liver Fibrosis stage at biopsy | | | | |
| F0 No | 62 (20%) | 0 (0%) | 16 (8%) | 8 (13%) |
| F1 Fibrosis without septa | 127 (41%) | 102 (60%) | 136 (68%) | 23 (37%) |
| F2 Few septa | 52 (17%) | 39 (23%) | 33 (16%) | 11 (18%) |
| F3 Many septa | 36 (11%) | 19 (11%) | 9 (4%) | 7 (11%) |
| F4 Cirrhosis | 33 (11%) | 11 (6%) | 7 (3%) | 13 (21%) |
| Markers (normal range) | | | | |
| AST IU/L (17-27 female; 20-32 male) | 83 (159) | 82 (57) | 23 (9) | 89 (83) |
| ALT IU/L (11-26 female; 16-35 male) | 109 (114) | 118 (94) | 19 (10) | 72 (88) |
| Total bilirubin mol/L (1-21) | 14.8 (26.2) | 11.1 (4.8) | 8.8 (4.6) | 21.5 (19.6) |
| GGT U/L (7-32 female; 11-49 male) | 112 (183) | 84 (96) | 21 (18) | 323 (443) |
| 2 macroglobulin g/L (female 1.6-4.0: male 1.4-3.3) | 2.4 (1.0) | 3.1 (1.2) | 2.0 (0.8) | 1.8 (0.5) |
| Apo A1 g/L (1.2-1.7) | 1.4 (0.3) | 1.3 (0.3) | 1.2 (0.3) | 1.5 (0.5) |
| Haptoglobin g/L (0.35-2.00)* | 0.95 (0.57) | 0.78 (0.45) | 0.86 (0.43) | 1.39 (0.63) |
| Glucose (mmol/L) | 5.5 (3.2) | 5.4 (1.2) | 5.3 (1.0) | 5.8 (1.6) |
| Cholesterol (mmol/L) | 4.9 (1.3) | 4.5 (1.0) | 5.0 (1.0) | 5.4 (1.9) |
| Triglycerides (mmol/L) | 1.5 (1.4) | 1.4 (0.8) | 1.6 (1.0) | 1.9 (3.1) |
| Fibro Test | 0.42 (0.28) | 0.47 (0.26) | 0.29 (0.20) | 0.43 (0.28) |
| Steato Test | 0.49 (0.25) | 0.53 (0.22) | 0.36 (0.22) | 0.58 (0.25) |

Data are mean (SD) or proportion.
AST = aspartate aminotransferase.
ALT = alanine aminotransferase.
GGT = glutamyl transpeptidase.
ApoA1 = apolipoprotein a1.

A control group was also analyzed. It was constituted of fasting and non-fasting apparently healthy volunteers previously included in a validation of FibroTest (Munteanu M, et al. Comp. Hepatol. 2004; 3,3) and additional non-fasting blood donors.

1.2. Serum Markers

The 10 following biochemical markers were assessed for the different groups: ApoA1, ALT (alanine aminotransferase), AST (aspartate aminotransferase), alpha.2-macroglobulin, GGT (gammaglutamyl transpeptidase), total bilirubin, haptoglobin, cholesterol, glucose, and triglycerides.

These 10 biochemical markers include the 6 components of the FibroTest-ActiTest adjusted by age and gender (patented artificial intelligence algorithm U.S. Pat. No. 6,631,330) plus the AST, cholesterol, glucose, and triglycerides markers and the BMI.

FibroTest (Biopredictive, Paris, France; FibroSURE LabCorp, Burlington, N.C., USA) was determined as previously published (Poynard T, et al. Comp Hepatol. 2004; 3:8; Myers R P, et al. J Hepatol. 2003; 39:222-30; Callewaert N, et al. Nature Med 2004; 10; 1-6; Naveau S, et al. Clin Gastroenterol Hepatol in press; Imbert-Bismut F, et al. Clin Chem Lab Med 2004; 42:323-33; Munteanu M, et al. Comp Hepatol 2004; 3:3).

The published recommended pre-analytical and analytical procedures were used (Poynard T, et al. Comp Hepatol. 2004; 3:8; Myers R P, et al. J Hepatol. 2003; 39:222-30; Callewaert N, et al. Nature Med 2004; 10; 1-6; Naveau S, et al. Clin Gastroenterol Hepatol in press; Imbert-Bismut F, et al. Clin Chem Lab Med 2004; 42:323-33; Munteanu M, et al. Comp Hepatol 2004; 3:3).

In the training and control groups GGT, ALT, serum glucose, triglycerides, cholesterol, and total bilirubin were measured by Hitachi 917 analyzer or Modular DP analyzers (both Roche Diagnostics Mannheim, Germany) using the manufacturer's reagents. Alpha2-macroglobulin, apolipoprotein A1, and haptoglobin were measured using an automatic nephelemeter BNII (Dade Behring; Marburg, Germany).

In validation groups 1 and 2, GGT, ALT, serum glucose, triglycerides, cholesterol, and total bilirubin were measured using Hitachi 747 or 911 (Roche Diagnostics, Indianapolis, Ind., USA) using the manufacturer's reagents. Apolipoprotein A1, alpha2-macroglobulin, and haptoglobin were determined in serum samples using an automatic nephelometer BNII (Dade Behring; Marburg, Germany).

In validation group 3, ALT, GGT, serum glucose, triglycerides, cholesterol, total bilirubin and haptoglobin were measured by autoanalyzer (Olympus AU 640 Automate) using manufacturer's reagents (Olympus, Rungis France); alpha2-macroglobulin and apolipoprotein A1 were measured using an automatic nephelometer (BNII, Dade Behring; Marburg, Germany).

All coefficients of variation assays were lower than 10%.

1.3. Histological Grading

Histological grading was performed based on liver biopsies. Common rules were applied in the different groups, and a single pathologist per group, unaware of patient characteristics, analyzed the histological features. Liver biopsy specimens were processed using standard techniques.

Hepatic steatosis was scored from 0 to 4 with a four grades scoring system: 0=no steatosis, 1 to 5%=mild, 6 to 32%=moderate, 33 to 66%=marked, 67-100%=severe, all percentages referring to the percentage of hepatocytes involved in steatosis (Poynard T, et al. Hepatology. 2003; 38:75-85). The main histological criterion was the presence of steatosis grade 2-4 (between 6 to 100%).

Example 2

Statistical Analysis

Statistical analysis used Fisher's exact test, the chi-square test, Student's t test, the Mann-Whitney test and variance analysis using the Bonferroni all-pair wise and Tukey-Kramer multiple-comparison tests to take into account the multiple comparisons and multiple logistic regression for multivariate analysis (Hintze J L. NCSS 2003 User Guide. Number Cruncher Statistical Systems 2003 software NCSS, Kaysville, Utah). The analysis was performed on a first group (training group) and validated on 3 different groups (validation groups 1, 2 and 3), in cohorts of patients as in Table 1.

According to the hepatic steatosis scoring system, patients were divided into several groups.

The primary outcome was the identification of patients with hepatic steatosis grade 2, 3 or 4 (moderate, marked or severe).

In a secondary analysis, patients were classified according to a 4 scale scoring system.

The first stage consisted of identifying factors which differed significantly between these groups by unidimensional analysis using the chi-square, Student t test or Mann-Whitney test.

The second stage consisted of logistic regression analysis to assess the independent discriminative value of markers for the diagnosis of fibrosis.

The third step was to construct an index combining these identified independent factors. By definition the best index ("Steatosis score") in term of discrimination was the logistic regression function combining the independent factors. In all the following examples, the Steatosis score is further referred to as "SteatoTest score". The SteatoTest score ranges from zero to 1.00, with higher scores indicating a greater probability of significant lesions.

The diagnostic values of the markers were assessed using sensitivities, specificities, positive (PPV) and negative predictive values (NPV), and the areas under the Receiver Operating characteristic (ROC) curves (Hintze J L. NCSS 2003 User Guide. Number Cruncher Statistical Systems 2003 software NCSS, Kaysville, Utah).

The respective overall diagnostic values were compared by the area under the ROC curves. The ROC curve is drawn by plotting the sensitivity versus (1-specificity), after classification of the patients, according to the value obtained for the logistic function, for different thresholds (from 0 to 1). It is usually acknowledged that a ROC curve the area under which has a value superior to 0.7 is a good predictive curve for diagnosis. The ROC curve has to be acknowledged as a curve allowing to predict the quality of a diagnosis method.

Areas under ROC curves were calculated using empirical non-parametric method. A sensitivity analysis was also performed to determine the accuracy of the markers for the primary outcomes according to biopsy sample size. For all analyses, two-sided statistical tests were used; a P-value of 0.05 or less was considered significant. Number Cruncher Statistical Systems 2003 software (NCSS, Kaysville, Utah) was used for all analyses (Hintze J L. NCSS 2003 User Guide. Number Cruncher Statistical Systems 2003 software NCSS, Kaysville, Utah).

These statistical analyses were performed separately for the different groups, as previously defined.

Example 3

Determination of the Logistic Function

The "SteatoTest score" is defined as the logistic regression function combining the independent factors that returns the best index in term of discrimination between the presence or absence of hepatic steatosis.

In Table 2 are given the characteristics of patients according to the presence of hepatic steatosis for each of the 10 biochemical markers, the FibroTest score, and the SteatoTest score, as well as their independent association with fibrosis (P value).

In the training group the most significant components associated with the presence of grade 2-4 steatosis in univariate analysis were BMI, age, ALT, AST, GGT, glucose, and triglycerides.

In logistic regression analysis the most significant components were BMI (OR=0.89 P=0.0002), GGT (OR=0.31 P=0.002), apolipoprotein A1 (OR=3.20 P=0.01), alpha2-macroglobulin (OR=5.74 P=0.02), ALT (OR=0.38 P=0.03) and triglycerides (OR=0.31 P=0.04).

In the validation group similar differences were observed, most significantly for BMI, GGT, ALT and triglycerides (Table 2).

TABLE 2

Characteristics of patients according to the presence of steatosis

| | Steatosis Training group | | | Steatosis Validation group 1 HCV pos | | |
|---|---|---|---|---|---|---|
| Characteristic | <5% n = 170 m(SD) | >=5% n = 140 | P value | No n = 126 | Yes n = 45 | P value |
| Demographics | | | | | | |
| Age at biopsy, years | 46.7 (12.4) | 51.8 (12.1) | 0.0004 | 43.7 (7.3) | 45.2 (7.0) | 0.28 |
| Male gender | 110 (55%) | 91 (45%) | 0.96 | 81 (64%) | 30 (67%) | 0.77 |
| BMI | 24 (4) | 27 (6) | <0.0001 | 27 (5) | 31 (4) | <0.0001 |
| Biochemical markers | | | | | | |
| $\alpha_2$-macroglobulin, g/L | 2.47 (1.00) | 2.30 (1.04) | 0.07 | 3.10 (1.23) | 3.20 (1.24) | 0.50 |
| ALT, IU/L | 104 (119) | 115 (108) | 0.02 | 46 (45) | 61 (48) | 0.003 |
| AST, IU/L | 83 (204) | 83 (78) | 0.01 | 80 (61) | 88 (43) | 0.01 |
| Apolipoprotein A1, g/L | 1.46 (0.34) | 1.42 (0.33) | 0.30 | 1.27 (0.26) | 1.20 (0.24) | 0.18 |
| Haptoglobin, g/L | 0.93 (0.60) | 0.96 (0.52) | 0.19 | 0.77 (0.45) | 0.78 (0.44) | 0.84 |
| GGT, IU/L | 83 (132) | 147 (226) | <0.0001 | 72 (85) | 118 (116) | 0.0007 |
| Total bilirubin, μmol/L | 14.8 (31.4) | 14.7 (17.8) | 0.47 | 11.0 (5.0) | 11.3 (4.1) | 0.38 |
| Glucose mmol/L | 5.1 (3.7) | 5.9 (2.2) | <0.0001 | 5.2 (0.9) | 6.0 (1.8) | 0.0007 |
| Triglycerides mmol/L | 1.24 (0.95) | 1.88 (1.78) | <0.0001 | 1.26 (0.72) | 1.72 (1.0) | 0.0008 |
| Total cholesterol mmol/L | 4.8 (1.2) | 5.1 (1.4) | 0.10 | 4.5 (1.0) | 4.4 (1.0) | 0.10 |
| Fibro Test | 0.40 (0.29) | 0.45 (0.28) | 0.47 | 0.45 (0.26) | 0.53 (0.24) | 0.07 |
| Steato Test | 0.38 (0.21) | 0.62 (0.22) | <0.0001 | 0.47 (0.21) | 0.70 (0.16) | <0.0001 |

| | Steatosis Validation group 2 HCV neg | | | Steatosis Validation group 3 Alcoholic liver disease | | |
|---|---|---|---|---|---|---|
| Characteristic | No n = 179 | Yes n = 22 | P value | <5% n = 4 m(SD) | >=5% n = 58 | P value |
| Demographics | | | | | | |
| Age at biopsy, years | 43.7 (8.1) | 43.1 (7.0) | 0.7 | 38.0 (12.8) | 47 (9.4) | 0.16 |
| Male gender | 110 (62%) | 12 (55%) | 0.53 | 2 (50%) | 45 (78%) | 0.21 |
| BMI | 26 (4) | 31 (6) | <0.0001 | 22.9 (2.9) | 24.3 (4.2) | 0.49 |
| Biochemical markers | | | | | | |
| $\alpha_2$-macroglobulin, g/L | 2.08 (0.79) | 1.73 (0.66) | 0.06 | 2.12 (0.53) | 1.81 (0.55) | 0.26 |
| ALT, IU/L | 18 (9) | 26 (9) | <0.0001 | 35 (24) | 74 (90) | 0.10 |
| AST, IU/L | 23 (9) | 25 (7) | 0.26 | 74 (43) | 58 (90) | 1.00 |
| Apolipoprotein A1, g/L | 1.16 (0.28) | 1.07 (0.25) | 0.2 | 1.67 (0.43) | 1.48 (0.49) | 0.49 |
| Haptoglobin, g/L | 0.85 (0.41) | 0.94 (0.56) | 0.85 | 1.55 (0.92) | 1.38 (0.62) | 0.85 |
| GGT, IU/L | 20 (18) | 28 (14) | 0.0002 | 327 (184) | 323 (323) | 0.41 |
| Total bilirubin, μmol/L | 8.9 (4.6) | 8.1 (4.3) | 0.3 | 28.5 (23.4) | 21.1 (19.5) | 0.28 |
| Glucose mmol/L | 5.3 (1.0) | 5.5 (0.8) | 0.16 | 6.5 (2.2) | 5.7 (1.6) | 0.46 |
| Triglycerides mmol/L | 1.49 (0.98) | 2.05 (1.22) | 0.003 | 1.05 (0.51) | 1.96 (3.15) | 0.28 |
| Total cholesterol mmol/L | 5.0 (1.0) | 5.1 (0.9) | 0.51 | 6.0 (1.38) | 5.4 (2.0) | 0.68 |
| Fibro Test | 0.29 (0.20) | 0.26 (0.19) | 0.46 | 0.43 (0.32) | 0.43 (0.28) | 0.79 |
| Steato Test | 0.32 (0.20) | 0.62 (0.17) | <0.0001 | 0.44 (0.03) | 0.59 (0.26) | 0.21 |

All data are means (sd) and proportions (n [%]). ALT, alanine aminotransferase; AST, aspartate aminotransferase; GGT, γ-glutamyl-transpeptidase.
Steato Test combines in a multivariate regression analysis adjusted for gender, age and body mass index: alanine and aspartate aminotransferases, alpha-macroglobulin, apolipoprotein A-I, haptoglobin, total bilirubin, and γ-glutamyl-transpeptidase The best logistic function (SteatoTest score) combining 9 markers and age, gender and BMI was determined on the training group to be as follows:

$f$=6.68805−1.55337$E$-02.[Age(years)]+1.161531. [ApoA1(g/L)]−0.11889.[Body Mass Index (Weight/Height$^2$)]+1.74791.Log [.alpha.2-macroglobulin(g/L)]−0.96453.Log [ALT(alanine aminotransferase)(TU/L)]−0.11958.Log [total bilirubin(μmol/L)]−0.68125.Log [cholesterol (mmol/L)]−1.17922.Log [GGT(gammaglutamyl transpeptidase)(IU/L)]−1.46963.Log [glucose (mmol/L)]−0.34512.Log [Haptoglobin(g/L)]−1.17926.Log [triglycerides(mmol/L)]+0.35052. [Gender(female=0,male=1)].

This function was obtained on the training group by combining the relative weight of each parameter, as individually determined in the logistic regression, with a negative sign when the markers harbors a negative correlation with the stage of hepatic steatosis. Logarithms were used for markers whose values have a very large range.

The value of the SteatoTest score, combining 9 markers (alpha2-macroglobulin, ALT, apo A1, haptoglobin, GGT, and total bilirubin), adjusted by age, gender and BMI, had a high correlation with the presence or absence of hepatic steatosis, on the training sample as well as on validation samples (Table 2).

One of the major discoveries of the present work is the very significant improvement in the diagnostic value of steatosis when combining markers versus the classical routine test previously recommended such as GGT and ALT. The simple markers of insulin resistance such as BMI, glucose, triglycerides increased the diagnostic value of ALT and GGT. This had not been previously demonstrated in the different causes of liver steatosis. Furthermore, it was demonstrated for the first time that the diagnostic value of ALT was much greater than GGT for the diagnosis of steatosis. Interestingly also, the GGT value did not increase according to the severity of steatosis in comparison to ALT.

Example 4

Analysis of the Data 4.1 Fiability of the SteatoTest Score for the Diagnosis of Hepatic Steatosis.

Diagnostic values (areas under ROC curves) of the SteatoTest score for the different patients groups are displayed in Table 3. Sensitivity, specificity and positive and negative predictive values of the SteatoTest score with a cut-off of 0.30, 0.50, and 0.70 are displayed in Table 4.

TABLE 3

Values [Area under the ROC curves (AUROCs)] of Steatosis score, GGT and ALT for the diagnosis of steatosis, in training and validation groups

| Diagnostic panel | Training group AUROC (se) N = 310 | Validation group 1 HCV detectable N = 171 | Validation group 2 HCV Undetectable N = 201 | Validation group 3 Alcoholic Liver Disease N = 62 |
|---|---|---|---|---|
| SteatoTest | 0.79 (0.03)* | 0.80 (0.04)£ | 0.86 (0.03)$ | 0.72 (0.05)** |
| GGT | 0.66 (0.03) | 0.67 (0.05) | 0.74 (0.05) | 0.50 (0.09) |
| ALT | 0.58 (0.03) | 0.62 (0.05) | 0.79 (0.04) | 0.66 (0.07) |

*Higher than GGT (p < 0.0001) and ALT (p < 0.0001)
£Higher than GGT (p = 0.007) and ALT (p < 0.0001)
$Higher than GGT (p = 0.02)
**Higher than GGT (p = 0.002)

TABLE 4

Diagnostic value of Steatosis score for predicting hepatic steatosis greater than 5%

| Cut-off | Sensitivity | Specificity | Positive Predictive Value | Negative Predictive Value |
|---|---|---|---|---|
| Training group N = 310 | | | Prevalence = 45% | |
| SteatoTest 0.30 | 0.91 (127/140) | 0.45 (77/170) | 0.58 (127/220) | 0.86 (77/90) |
| 0.50 | 0.69 (97/140) | 0.74 (126/170) | 0.69 (97/141) | 0.75 (126/169) |
| 0.70 | 0.45 (63/140) | 0.89 (152/170) | 0.78 (63/81) | 0.66 (152/229) |
| GGT 50 IU/L | 0.66 (92/140) | 0.55 (94/170) | 0.55 (92/168) | 0.66 (94/142) |
| ALT 50 IU/L | 0.77 (108/140) | 0.35 (60/170) | 0.50 (108/218) | 0.65 (60/92) |
| Validation group1 N = 171 | | | Prevalence = 26% | |
| SteatoTest 0.30 | 0.98 (44/45) | 0.24 (30/126) | 0.31 (44/140) | 0.97 (30/31) |
| 0.50 | 0.89 (40/45) | 0.58 (73/126) | 0.43 (40/93) | 0.94 (73/78) |
| 0.70 | 0.44 (20/45) | 0.83 (105/126) | 0.49 (20/41) | 0.81 (105/130) |
| GGT 50 IU/L | 0.62 (28/45) | 0.61 (72/126) | 0.34 (28/82) | 0.81 (72/89) |
| ALT 50 IU/L | 1.00 (45/45) | 0.06 (8/126) | 0.28 (45/163) | 1.00 (8/8) |
| Validation group2 N = 201 | | | Prevalence = 11% | |
| SteatoTest 0.30 | 1.00 (22/22) | 0.56 (100/179) | 0.22 (22/101) | 1.00 (100/100) |
| 0.50 | 0.68 (15/22) | 0.79 (142/179) | 0.29 (15/52) | 0.95 (142/149) |
| 0.70 | 0.32 (7/22) | 0.92 (165/179) | 0.33 (7/21) | 0.92 (165/180) |
| GGT 50 IU/L | 0.09 (2/22) | 0.97 (174/179) | 0.29 (2/7) | 0.90 (174/194) |
| ALT 50 IU/L | 0.05 (1/22) | 0.98 (176/179) | 0.25 (1/3) | 0.89 (176/197) |
| Validation group3 N = 62 | | | Prevalence = 94% | |
| SteatoTest 0.30 | 0.85 (49/58) | 0.00 (0/4) | 0.93 (49/53) | 0.00 (0/9) |
| 0.50 | 0.62 (36/58) | 1.00 (4/4) | 1.00 (36/36) | 0.15 (4/26) |
| 0.70 | 0.40 (23/58) | 1.00 (4/4) | 1.00 (23/23) | 0.10 (4/39) |
| GGT 50 IU/L | 0.90 (52/58) | 0.00 (0/4) | 0.93 (52/56) | 0.00 (0/6) |
| ALT 50 IU/L | 0.53 (31/58) | 0.75 (3/4) | 0.97 (31/32) | 0.10 (3/30) |

All the results show that the SteatoTest score can reach very high diagnostic values (area under the ROC curve, see Table 3), and high specificity, sensitivity and positive or negative predictive values for the diagnosis of hepatic steatosis (see Table 4).

Figure 2A:
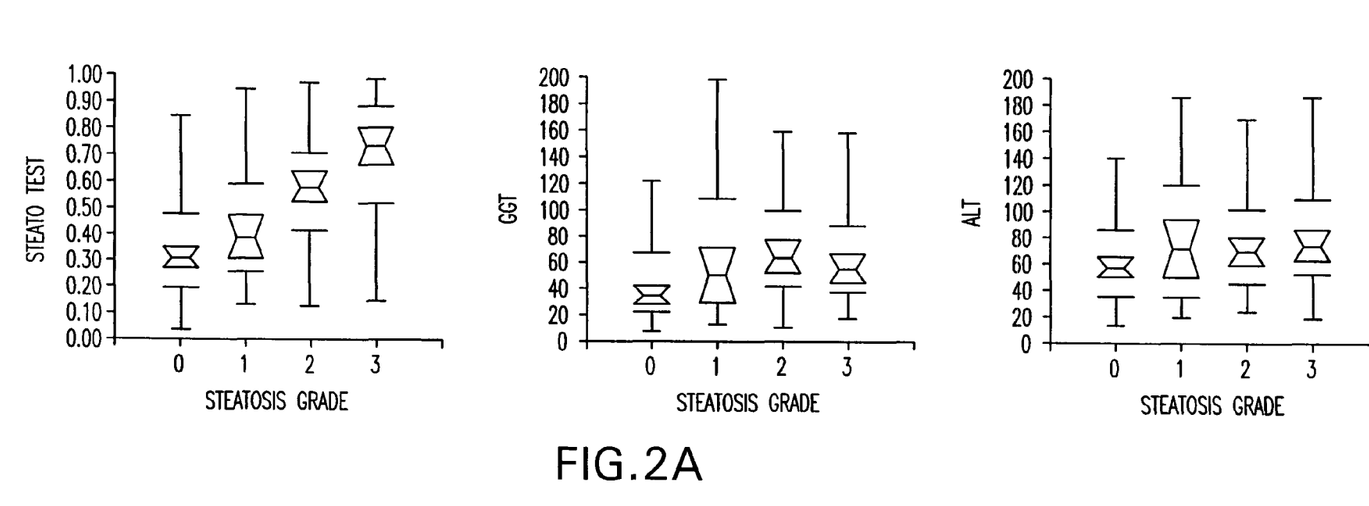
Figure 2B:
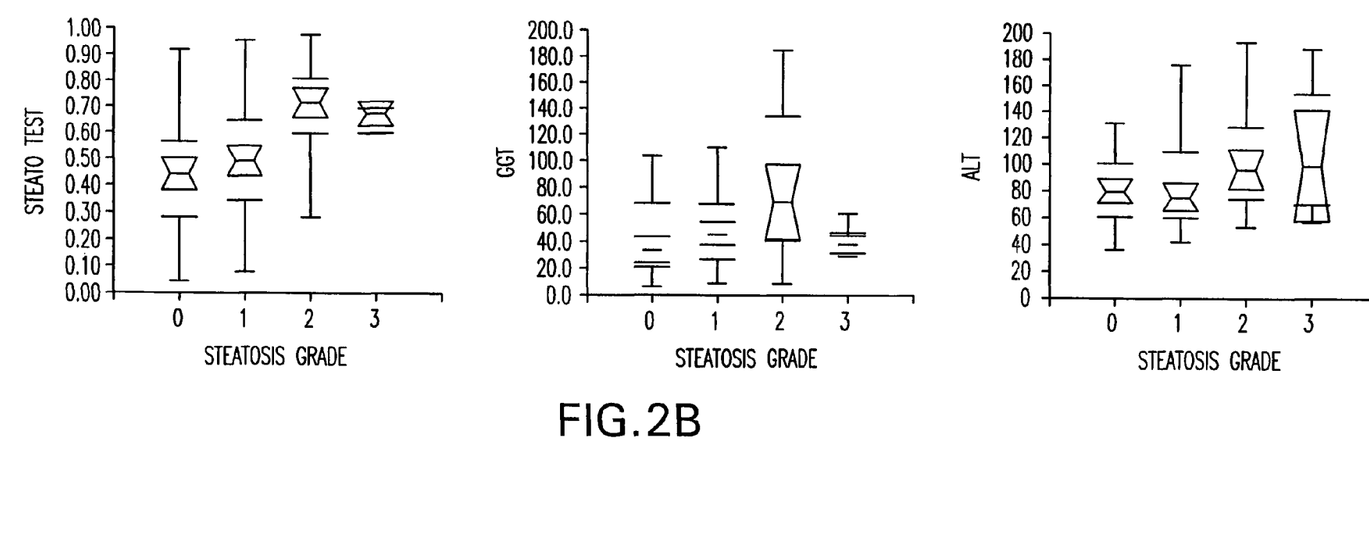
Figure 2C:
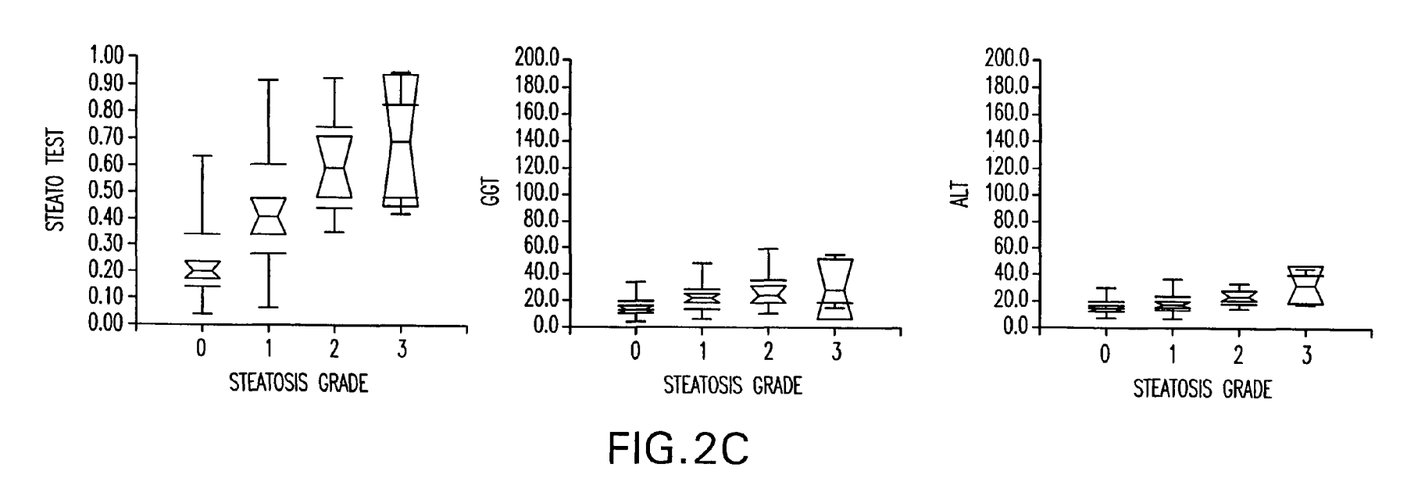
Figure 2D:
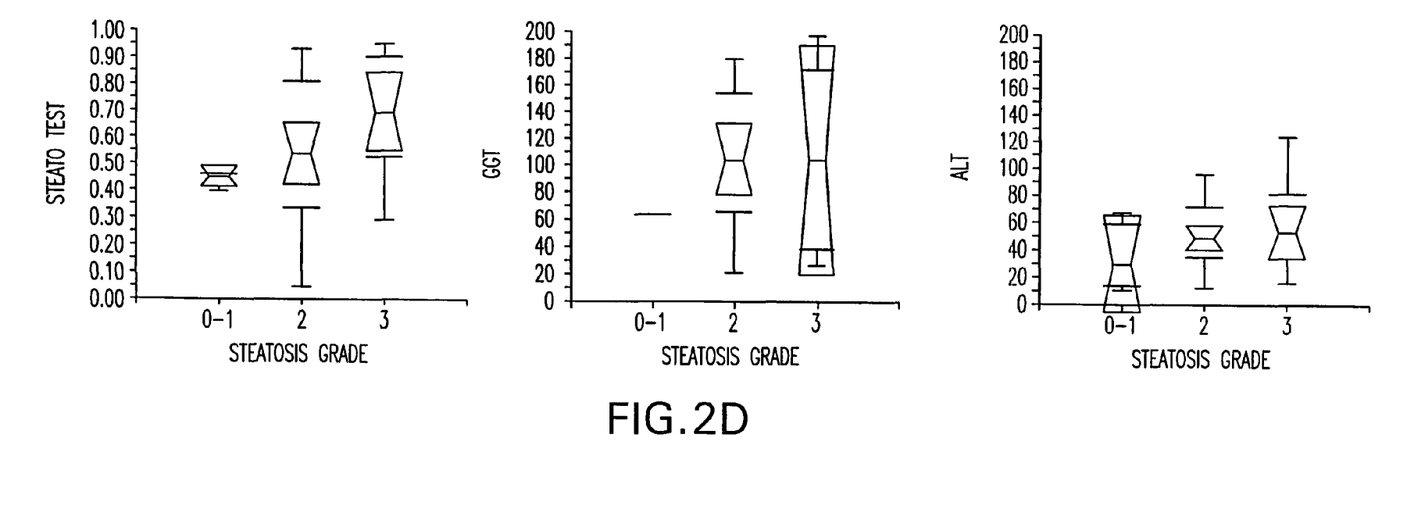
Figure 2E:
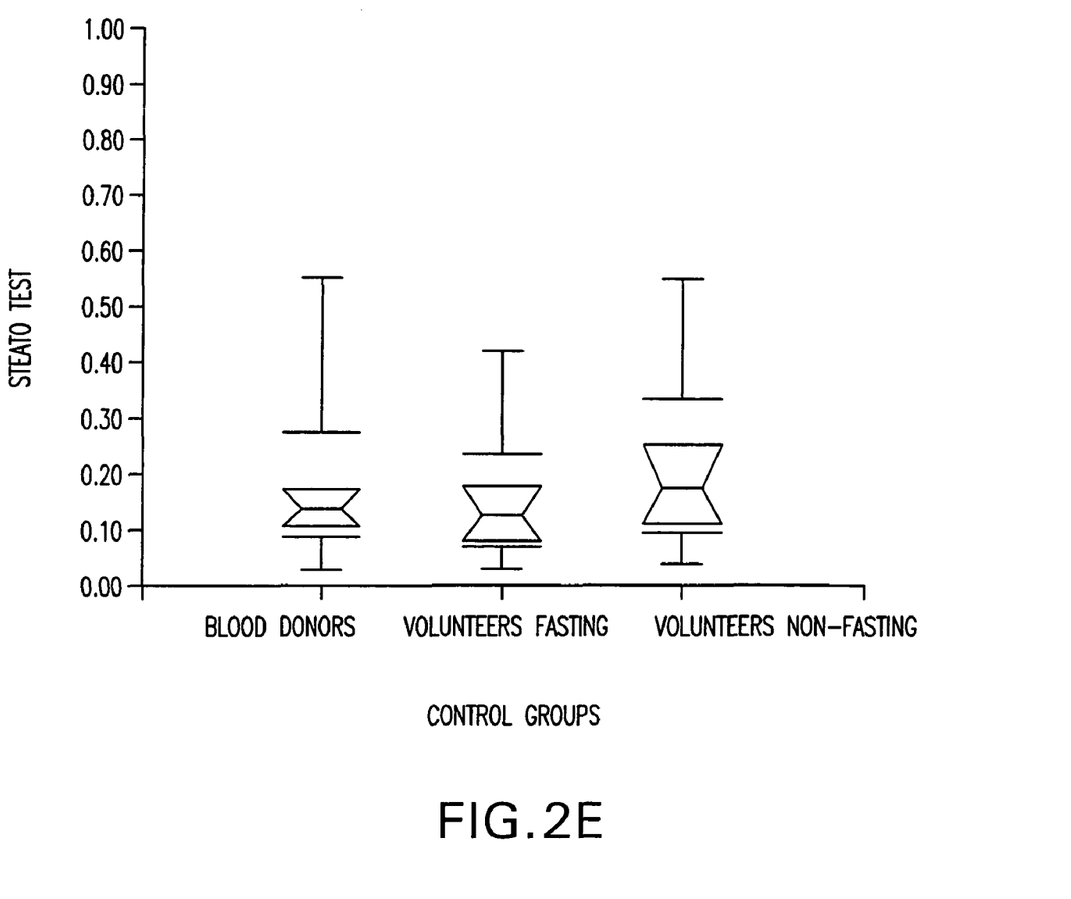

The diagnostic value (area under the ROC curve) of the SteatoTest score was highly reproducible between the training group and validation groups 1, 2 and 3 (Table 3). The sensitivity was also quite reproducible between the training group and validation groups 1, 2 and 3 (Table 4). In addition, the sensitivities and specificities of the SteatoTest score observed in the different populations studied will probably increase in a more general population because of the excellent specificity observed in volunteers and blood donors (FIG. 2E), and because of the fact that the present studies have included a limited number of patients with several metabolic risk factors such as morbid obesity.

For some patients, the diagnoses of the presence of hepatic steatosis by biopsy and by the SteatoTest score were discordant. The cause of discordance between presence of >5% hepatic steatosis predicted by biochemical markers and biopsy was attributed according to respective risk factors of failure as previously detailed (Poynard T, et al. Clin. Chem. 2004; 50:1344-55). Significant discordance was defined as discordance in predicting 5>% hepatic steatosis (grades 2-4) and a 30% or greater difference in >5% hepatic steatosis percentage as predicted by the SteatoTest score or as observed in the biopsy sample. Risk factors of SteatoTest score failure were hemolysis, Gilbert's disease, acute inflammation and extra hepatic cholestasis. Risk factors of biopsy failure were biopsy size (less than 25 mm) and fragmentation (more than one fragment). Failure attributable to biopsy (false negative) was suspected when the biopsy was smaller than 15 mm and fragmented plus the presence of at least one metabolic risk factor.

In the training group there were 56 cases (18%) of significant discordance between steatosis percentage as predicted by ST and that observed in biopsy samples. Failure attributable to ST (false positive of ST) was suspected in one case that had acute drug hepatitis associated with chronic hepatitis B. Failure attributable to biopsy (false negatives of biopsy) was suspected in 16 cases with poor quality biopsy samples (median length 13 mm, 2 fragments) and at least one metabolic risk factor.

For the validation' groups, significant discordance was observed in 17 cases (16%) in group 1, 20 cases (10%) in group 2 and 13 cases (21%) in group 3. Significant discordance was observed more often in patients with extensive fibrosis (stage F3 or F4): 38 cases out of 135 (28%) versus 91 cases out of 609 (15% P=0.001).

Compared to the invasive and costly biopsy diagnosis, it is very important to notice that the method of the invention does not lead to a large number of undue treatments of patients or to the exclusion of patients in need of a treatment. The data presented in this application does strengthen the reliability of the method of diagnosis according to the present invention.

4.2 Comparison of the SteatoTest Score with Other Non Invasive Diagnosis Tests (Fibrotest, GGT 50 IU/L et ALT 50 IU/L)

The results obtained with the SteatoTest score (using 9 biochemical parameters adjusted by age, gender and BMI) were compared to those obtained with the use of isolated markers such as GGT and ALT, which are usually considered to be useful markers to indicate the presence or absence of hepatic steatosis. The same standard cut-off value is used for GGT and ALT: 50 IU/L. Under said cut-off value, the diagnostic of hepatic steatosis is considered to be negative, over, it is considered to be positive.

The characteristics of patients according to the presence of hepatic steatosis for individual biochemical markers, the FibroTest, and the SteatoTest score are displayed in Table 2.

Compared with FibroTest, the SteatoTest score allows a much better discrimination between the presence or absence of hepatic steatosis in all groups analyzed, in particular for the training group and validation group 2 (Table 2).

Diagnostic values (areas under ROC curves) of the SteatoTest score, GGT 50 IU/L and ALT 50 IU/L for the diagnosis of the main end point (that is, grade 2-4 hepatic steatosis), are displayed in Table 3. The SteatoTest score has higher areas under ROC curves than GGT 50 IU/L in all groups analyzed, and that ALT 50 IU/L in the training group and validation group 1 (Table 3).

Sensitivity, specificity and positive and negative predictive values of the SteatoTest score with a cut-off of 0.30, 0.50, or 0.70, and of GGT 50 IU/L and ALT 50 IU/L are displayed in Table 4. For the diagnosis of grade 2-4 steatosis, a SteatoTest score with a 0.50 cut-off achieved a good sensitivity (0.69, 0.89, 0.68 and 0.62) and a good specificity (0.74, 0.58, 0.79, 1.00), according to training and validation groups respectively. Moreover, such a SteatoTest score with a 0.50 cut-off displays higher positive and negative values than GGT 50 IU/L and ALT 50 IU/L in all groups analyzed, excepted for the negative predictive value of ALT 50 IU/L in validation group 1.

In addition, concerning the discrimination between hepatic steatosis different grades, it is best achieved by the SteatoTest score, compared to GGT 50 IU/L and ALT 50 IU/L in all groups analyzed (FIG. 2).

The discrimination between hepatic steatosis different grades was also analyzed on an integrated base constituted of all the included subjects of the training group, the three validation groups and the control group (884 subjects).

Figure 3:
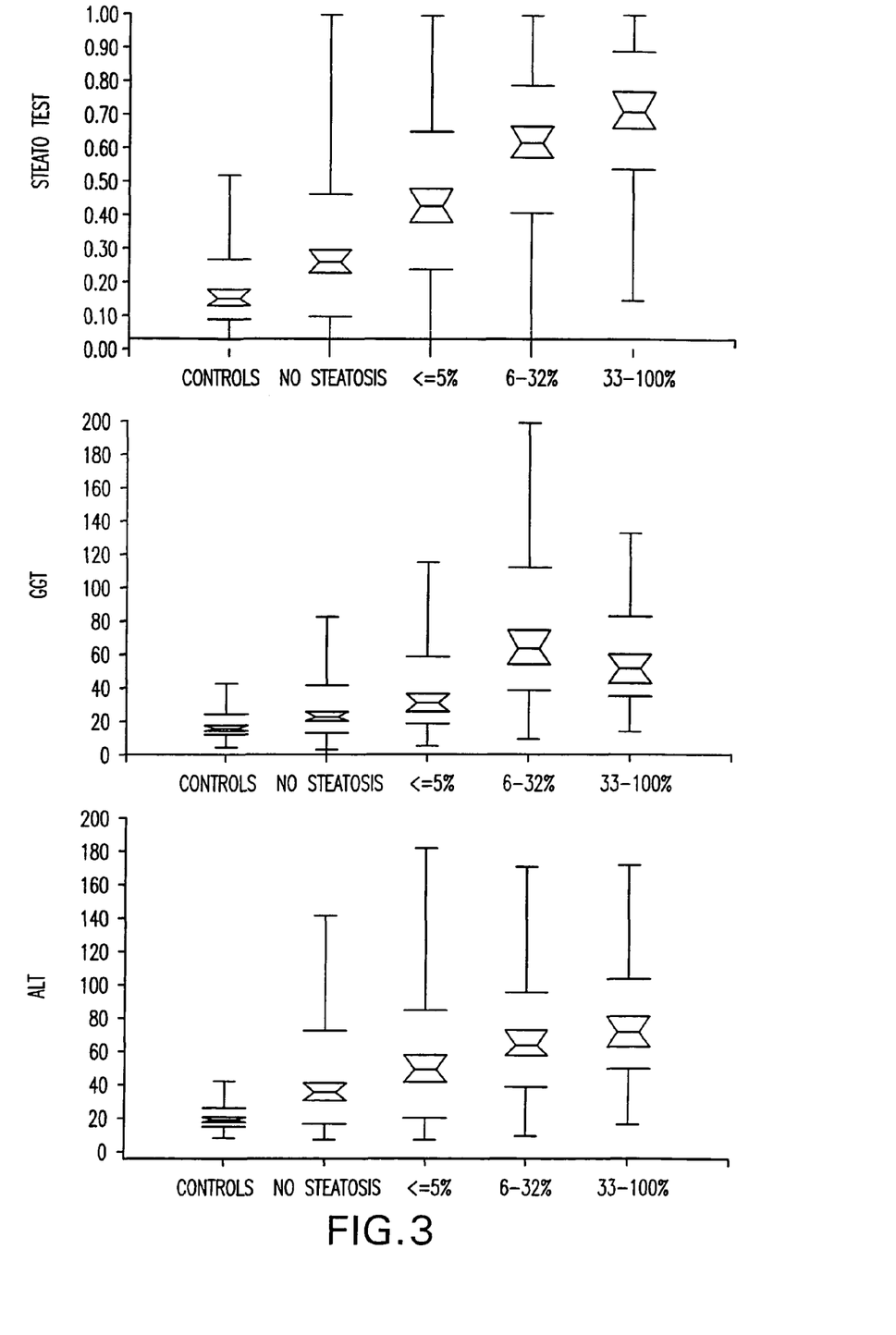
FIG. 3: Relationship between SteatoTest, GGT (IU/L) and ALT (IU/L) and the grade of liver steatosis in the integrated database combining controls, training group and validation groups.

There was a very significant overall correlation between the SteatoTest score and the steatosis grades from controls to "33-100%" (grades 3-4, see FIG. 3). For the SteatoTest score, there was a significant difference between all grades by Tukey-Kramer multiple comparison test for all pairwise differences between means (P<0.05). In contrast, for GGT and ALT, there was no significant difference between "No steatosis" (grade 0) and "<5%" (grade 1). For ALT, there was even no significant difference between "No steatosis" (grade 0) and "6-32%" (grade 2), "<5%" (grade 1) and "6-32%" (grade 2), and "6-32%" (grade 2) and "33-66%" (grade 3).

In conclusion, the present invention presents a combination of at least 5, preferably 9, biochemical markers, adjusted by age, gender and BMI, to be used for the detection of the presence or absence of hepatic steatosis. The markers used in the present invention had never been combined in such a way, particularly with the age, gender, and BMI of the patients to give such a good predictive value, as illustrated by the area under the ROC curve.

The diagnosis method of the invention can be analyzed automatically, after an automatic measurement of the values of the markers, and can advantageously be applied for patients with a hepatic steatosis involving disease to reduce the indication of liver biopsy.

The invention claimed is:

1. A method for diagnosis of hepatic steatosis in a patient or from a serum or plasma sample of a patient, comprising the steps of:

a) determining the value of 9 biochemical markers by measuring the values of their concentration in the serum or plasma of said patient, wherein said markers are:
ApoA1 (apolipoprotein A1),
alpha.2-macroglobulin,
ALT (alanine aminotransferase),
GGT (gammaglutamyl transpeptidase),
Triglycerides,
total bilirubin,
haptoglobin,
glucose, and
cholesterol;
b) determining the value of one clinical marker chosen in the group constituted of the body mass index (Weight/Height$^2$), the waist measurement, and the (waist measurement/hip measurement) ratio;
c) combining the concentration values of the 9 biochemical markers of step a), one clinical marker of step b), and the age and gender of the patient through a logistic function in order to obtain an end value, wherein said logistic function is obtained through the following method:
  i) classification of a cohort of patients in different groups according to the extent of their disease;
  ii) identification of factors which differ significantly between these groups by unidimensional analysis;
  iii) logistic regression analysis to assess the independent discriminative value of markers for the diagnosis of hepatic steatosis;
  iv) construction of the logistic function by combination of the identified independent factors; and
d) analyzing said end value of said logistic function in order to determine the presence of hepatic steatosis in said patient.

2. The method of claim 1, wherein said logistic function is:

$$f = a1 - a2.[\text{Age(years)}] + a3.[\text{ApoA1(g/L)}] - a4[\text{Body Mass Index(Weight/Height}^2)] + a5.\text{Log}[.\text{alpha.2-macroglobulin(g/L)}] - a6.\text{Log}[\text{ALT(alanine aminotransferase)(IU/L)}] - a7.\text{Log}[\text{total bilirubin}(\mu\text{mol/L})] - a8.[\text{cholesterol(mmol/L)}] - a9.\text{Log}[\text{GGT(gammaglutamyl transpeptidase)(IU/L)}] - a10.[\text{glucose(mmol/L)}] - a11.\text{Log}[\text{Haptoglobin(g/L)}] - a12.[\text{triglycerides(mmol/L)}] + a13.[\text{Gender(female=0,male=1)}], \text{with}$$

a1 comprised in the interval of [6.68805−90%; 6.68805+90%],
a2 comprised in the interval of [1.55337E-02−90%; 1.55337E-02+90%],
a3 comprised in the interval of [1.161531−90%; 1.161531+90%],
a4 comprised in the interval of [0.11889−90%; 0.11889+90%],
a5 comprised in the interval of [1.74791−90%; 1.74791+90%],
a6 comprised in the interval of [0.96453−90%; 0.96453+90%],
a7 comprised in the interval of [0.11958−90%; 0.11958+90%],
a8 comprised in the interval of [0.68125−90%; 0.68125+90%],
a9 comprised in the interval of [1.17922−90%; 1.17922+90%],
a10 comprised in the interval of [1.46963−90%; 1.46963+90%],
a11 comprised in the interval of [0.34512−90%; 0.34512+90%],
a12 comprised in the interval of [1.17926−90%; 1.17926+90%], and
a13 comprised in the interval of [0.35052−90%; 0.35052+90%].

3. The method of claim 2, wherein said logistic function is:

$$f = 6.68805 - 1.55337E\text{-}02.[\text{Age(years)}] + 1.161531.[\text{ApoA1(g/L)}] - 0.11889.[\text{Body Mass Index (Weight/Height}^2)] + 1.74791.\text{Log}[.\text{alpha.2-macroglobulin(g/L)}] - 0.96453.\text{Log}[\text{ALT(alanine aminotransferase)(IU/L)}] - 0.11958.\text{Log}[\text{total bilirubin}(\mu\text{mol/L})] - 0.68125.\text{Log}[\text{cholesterol(mmol/L)}] - 1.17922.\text{Log}[\text{GGT(gammaglutamyl transpeptidase)(IU/L)}] - 1.46963.\text{Log}[\text{glucose(mmol/L)}] - 0.34512.\text{Log}[\text{Haptoglobin(g/L)}] - 1.17926.\text{Log}[\text{triglycerides(mmol/L)}] + 0.35052.[\text{Gender(female=0,male=1)}].$$

4. The method of claim 1, wherein said end value of the logistic function is further used for the diagnosis of hepatic steatosis grade.

5. The method of claim 4, wherein said grade of hepatic steatosis is used to predict the evolution of the disease.

6. The method of claim 4, wherein said grade of hepatic steatosis is used for the choice of a suitable treatment for the patient.

7. The method of claim 4, wherein said grade of hepatic steatosis is used in the decision of performing a liver biopsy on said patient.

8. The method of claim 1, wherein said patient suffers from a disease involving hepatic steatosis.

9. The method of claim 8, wherein said disease is included in the group consisting of hepatitis B and C, alcoholism, hemochromatosis, metabolic disease, diabetes, obesity, autoimmune liver disease, primary biliary cirrhosis, alpha.1-antitrypsin deficit, and Wilson disease.

10. The method of claim 1, wherein said patient was already subjected to a diagnosis test of liver fibrosis and/or presence of liver necroinflammatory lesions.

11. The method of claim 10, wherein said diagnosis test was FibroTest/Acti-Test.

* * * * *